US008563800B2

(12) United States Patent
Smith

(10) Patent No.: US 8,563,800 B2
(45) Date of Patent: Oct. 22, 2013

(54) METHOD OF USE OF A TULIP-SHAPED SACRAL WOUND DRESSING

(76) Inventor: Patricia A. Smith, McCalla, AL (US)

( * ) Notice: Subject to any disclaimer, the term of this patent is extended or adjusted under 35 U.S.C. 154(b) by 639 days.

(21) Appl. No.: 12/620,067

(22) Filed: Nov. 17, 2009

(65) Prior Publication Data

US 2010/0125234 A1  May 20, 2010

Related U.S. Application Data

(60) Provisional application No. 61/199,523, filed on Nov. 18, 2008.

(51) Int. Cl.
*A61F 15/00* (2006.01)
(52) U.S. Cl.
USPC ............... 602/56; 602/41; 602/42; 602/43; 602/52; 602/54; 602/57; 602/58; 602/61; 128/888; 128/889; D24/188; D24/189; 424/445; 604/304

(58) Field of Classification Search
USPC ............. 602/41–43, 52, 54, 56, 57, 58, 61; 128/888–889, 891–892; D24/188, 189; D1/100–199; D20/11; 424/443–449; 604/304–306
See application file for complete search history.

(56) References Cited

U.S. PATENT DOCUMENTS

| | | | |
|---|---|---|---|
| 806,031 A | 11/1905 | Weber | |
| D113,676 S * | 3/1939 | Mastin | D24/189 |
| 2,685,086 A | 8/1954 | Henry | |
| 5,266,371 A | 11/1993 | Sugii et al. | |
| 5,704,905 A * | 1/1998 | Jensen et al. | 602/58 |
| 5,827,213 A | 10/1998 | Jensen | |
| D404,134 S | 1/1999 | Dunshee | |
| D432,656 S | 10/2000 | Nash et al. | |
| D433,142 S * | 10/2000 | Nash et al. | D24/189 |
| 6,264,976 B1 | 7/2001 | Heinecke et al. | |
| D454,956 S * | 3/2002 | Visintainer | D24/189 |
| 6,436,432 B2 | 8/2002 | Heinecke et al. | |
| D474,842 S | 5/2003 | Wolsing et al. | |
| D480,144 S | 9/2003 | Adams et al. | |
| D484,601 S | 12/2003 | Griffiths et al. | |
| D484,602 S | 12/2003 | Griffiths et al. | |
| 7,049,478 B1 | 5/2006 | Smith | |
| D524,946 S | 7/2006 | Shaw et al. | |
| D537,948 S | 3/2007 | Smith | |
| 7,217,853 B2 | 5/2007 | Kulichikhin et al. | |

OTHER PUBLICATIONS

MPM Medical, Inc.; Nov. 19, 2010; "Tulip Sacral Ulcer Wound Dressing"; pp. 1-2; www.mpmmedicalinc.com.*

* cited by examiner

*Primary Examiner* — Patricia Bianco
*Assistant Examiner* — Caitlin Carreiro
(74) *Attorney, Agent, or Firm* — Kenneth M. Bush; Bush Intellectual Property Law

(57) ABSTRACT

A sacral wound dressing having a bottom end with three substantially V-shaped projections. In use, a protective layer of the wound dressing is removed to expose an adhesive layer and an absorbent layer, the wound dressing is folded over on itself substantially along a central axis, a medial V-shaped projection is inserted into a superior portion of the gluteal cleft of the person to adhere the medial projection to the skin within the gluteal cleft, two lateral V-shaped projections are then pushed against a superior portion of the buttocks of the person to adhere the lateral projections to the skin, and the opposing lateral ends and the top end of the wound dressing are then pushed against the skin of the person until the wound dressing is properly adhered to the sacrococcygeal region over the sacral wound.

6 Claims, 4 Drawing Sheets

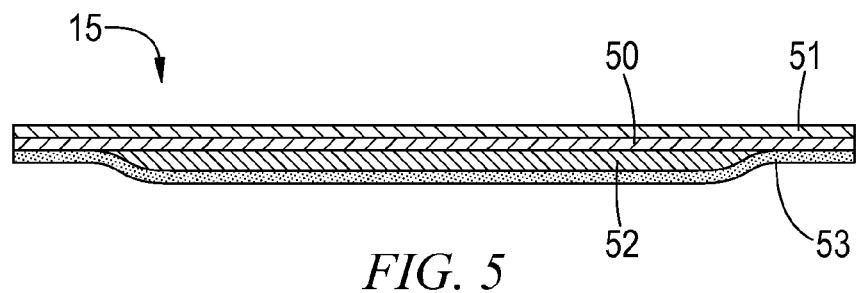
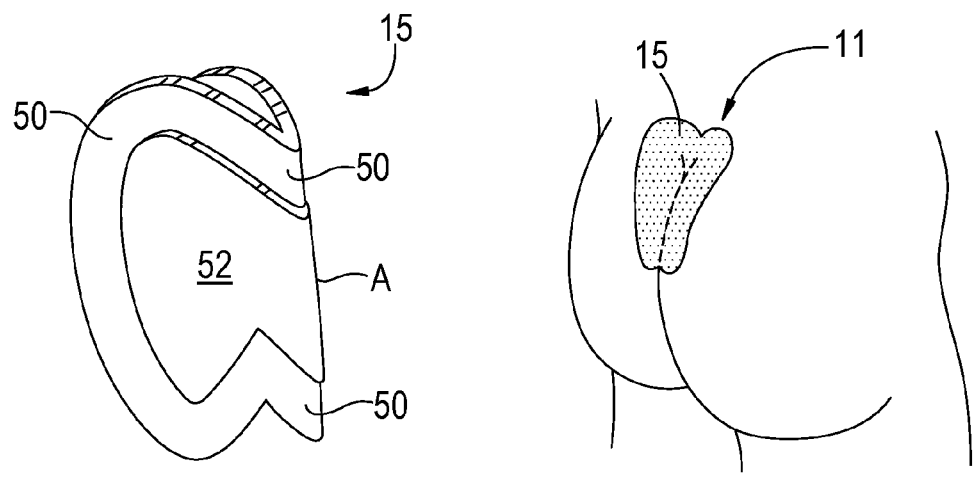 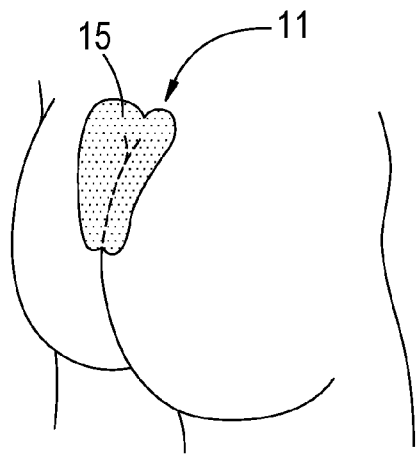

METHOD OF USE OF A TULIP-SHAPED SACRAL WOUND DRESSING

CROSS-REFERENCE TO RELATED APPLICATION

The present application claims priority to U.S. Provisional Patent Application No. 61/199,523 filed Nov. 18, 2008, the disclosure of which is incorporated herein by reference.

FIELD OF THE INVENTION

The present invention is related to adhesive wound dressings, and more particularly, to a wound dressing for securely covering a sacral wound.

BACKGROUND OF THE INVENTION

Pressure sores or wounds are injuries to the skin and/or the tissues under the skin. These types of wounds commonly form on persons confined to a chair or bed. Pressure wounds can range from red areas on the surface of the skin to severe tissue damage that goes deep into muscle and bone. Constant pressure on an area of skin reduces blood supply to that area and, over time, can break down the skin and form an open sore. Pressure wounds usually form on the skin over bony areas where there is little tissue between the bone and the skin. A common place for pressure wounds to form is in the lower back above the sacrum and coccyx. Treatment of these "sacral" wounds includes keeping the wound clean and covered with wound dressings.

A problem with current sacral wound dressings is that they do not adequately protect a sacral wound from contaminants, such as urine and feces. This is primarily due to insufficient sealing of the wound dressing to the skin around the wound. This occurs because of the anatomy of the sacrococcygeal body region. Specifically, the buttocks are separated by a gluteal cleft, sometimes also referred to as a gluteal fold or gluteal crease, which terminates at its superior end in the sacrococcygeal region. Sacral wounds frequently extend into the gluteal cleft. To adequately protect a sacral wound, a wound dressing should cover the superior end of the gluteal cleft and be pushed into the gluteal cleft to adhere to the skin, thereby creating a sealed protective zone around the sacral wound. However, prior art sacral wound dressings are not adequately designed for the anatomy of the sacrococcygeal region and, as a result, they tend to detach from the gluteal cleft as a result of patient movement, thus allowing contaminants to invade the protective zone and interfere with healing of the sacral wound.

Accordingly, what is needed, and is not found in the prior art, is a sacral wound dressing that will properly conform to the anatomy of the sacrococcygeal region of the body to provide a proper seal around a sacral wound and thereby prevent contaminants from invading the area protected by the dressing.

SUMMARY OF THE INVENTION

The present invention comprises a wound dressing for protecting a sacral wound in the sacrococcygeal region of a person. The preferred embodiment of the wound dressing comprises a top end, a bottom end having three substantially V-shaped projections wherein the projections include two lateral projections and a medial projection, opposing lateral ends, an adhesive layer, a backing layer adjacent the adhesive layer on an exterior side thereof, an absorbent layer adjacent the adhesive layer on an interior side thereof, and a removable protective layer attached to the adhesive layer on the interior side thereof so that the protective layer covers the absorbent layer.

In use, the protective layer of the wound dressing is removed to expose the adhesive layer and the absorbent layer, the wound dressing is folded over on itself substantially along a central axis running from the top end to the bottom end of the wound dressing so that the adhesive layer and the absorbent layer are outwardly oriented, the medial projection of the wound dressing is inserted into a superior portion of the gluteal cleft of the person to adhere the medial projection to the skin of the person within the gluteal cleft, the lateral projections of the wound dressing are then pushed against a superior portion of the buttocks of the person to adhere the lateral projections to the skin of the person, and the opposing lateral ends and the top end of the wound dressing are then pushed against the skin of the person until the wound dressing is properly adhered to the sacrococcygeal region of the person over the sacral wound. The wound dressing is reversibly adhered to the skin, thus the dressing can be repeatedly peeled back to inspect the wound and then resealed over the wound.

These and other features of the invention will become apparent from the following detailed description of the invention.

BRIEF DESCRIPTION OF THE DRAWINGS

FIG. 5 is a sectional view of the sacral wound dressing.

FIG. 6 is a perspective view of the sacral wound dressing folded over prior to application to the sacrococcygeal region of a person's body.

FIG. 7 is a perspective view of the sacral wound dressing secured to the sacrococcygeal region of a person's body.

DETAILED DESCRIPTION OF THE INVENTION

Figure 1:
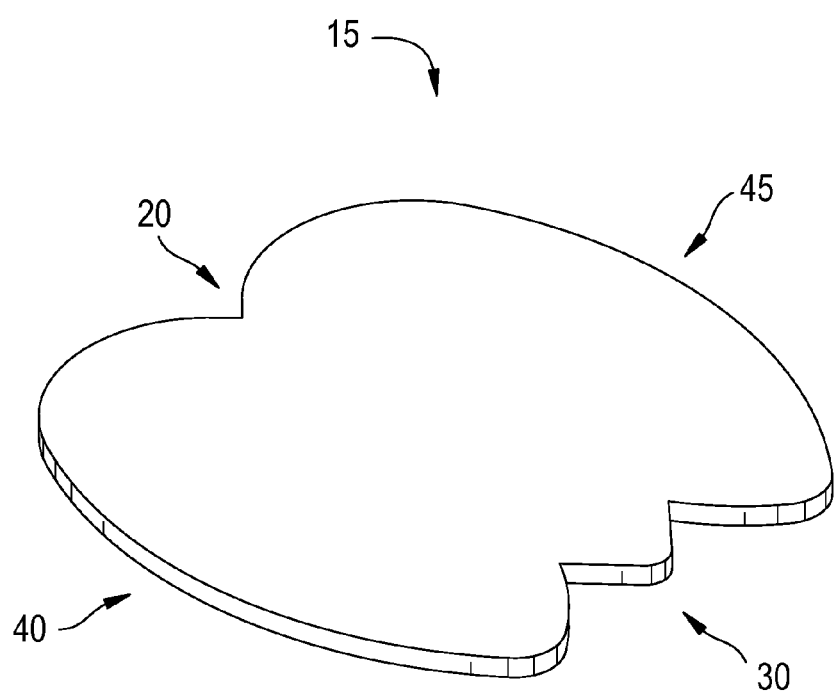
FIG. 1 is a perspective view of the preferred embodiment of the sacral wound dressing of the present invention.
Figure 2:
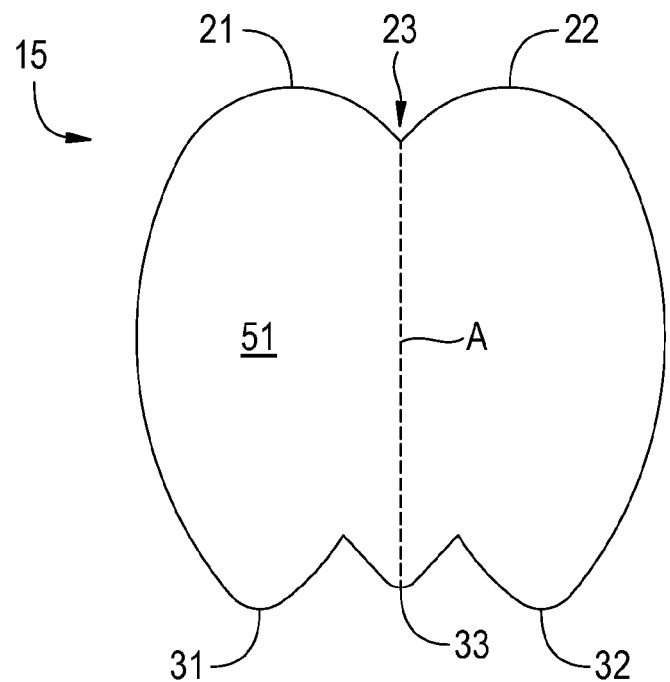
FIG. 2 is an exterior elevational view of the sacral wound dressing.
Figure 3:
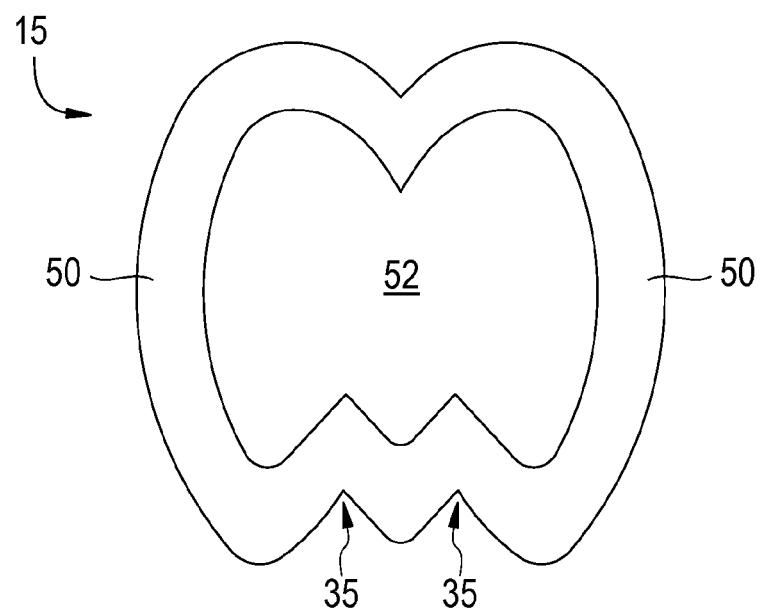
FIG. 3 is an interior elevational view of the sacral wound dressing.
Figure 4:
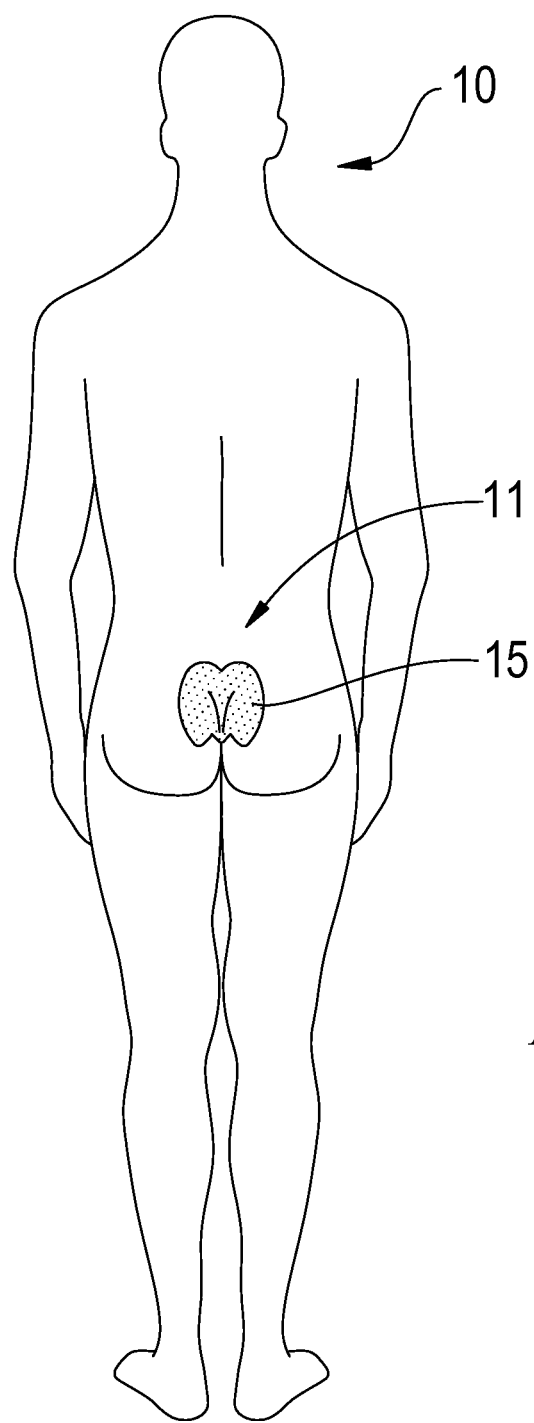
FIG. 4 shows the sacral wound dressing secured to the sacrococcygeal region of a person's body.

The preferred embodiment of the present invention is shown in FIGS. 1-7, wherein the invention comprises a wound dressing 15 for protecting a sacral wound in the sacrococcygeal region 11 of a person 10. The preferred embodiment of the wound dressing 15 comprises a top end 20, a bottom end 30, opposing lateral ends 40, 45, an adhesive layer 50, a backing layer 51, an absorbent layer 52, and a removable protective layer 53.

The top end 20 preferably comprises two substantially arcuate lobes 21, 22 that connect at a midpoint 23 along the top end 20, wherein the midpoint 23 is preferably indented so that the top end 20 better conforms to the shape of the body region to secure the top end 20 against the skin and thereby prevent inadvertent detachment from the skin. The bottom end 30 preferably comprises three substantially V-shaped or U-shaped projections (referred to herein as "V-shaped" projections), wherein the V-shaped projections include two lateral projections 31, 32 and a medial projection 33, wherein the lateral projections 31, 32 are preferably coextensive and a maximum length of the lateral projections 31, 32 is preferably greater than a maximum length of the medial projection 33. The medial projection 33 serves as an anchor for the wound dressing 15 and is designed to be secured within the superior portion of the gluteal cleft of a person 10. The spaces 35 between the projections 31, 32, 33 allow the bottom end 30 of the wound dressing 15 to flex considerably and thereby withstand substantial body movement, thus preventing inadvertent detachment from the skin. The opposing lateral ends 40, 45 are both preferably arcuate.

The adhesive layer 50 comprises an adhesive material that allows for reversible attachment of the wound dressing 15 to the skin. These types of adhesives are well known in the art of wound dressings. The backing layer 51 preferably comprises a waterproof material that allows gaseous exchange therethrough. These types of backings are well known in the art of wound dressings. The absorbent layer 52 preferably comprises a material capable of absorbing a large volume of exudate, thus allowing the wound dressing 15 to be used for up to 3-5 days. These types of absorbents are well known in the art of wound dressings. The removable protective layer 53 is preferably a thin paper or plastic that is reversibly bonded to the adhesive layer 50. These types of removable protective layers are well known in the art of wound dressings. The adhesive layer 50, backing layer 51, and absorbent layer 52 are all very flexible so as to conform to the shape of the body region and withstand substantial body movement without inadvertent detachment from the skin. In an alternate embodiment, the adhesive material and the absorbent material can be combined into a single layer, as is known in the art. Examples of materials used in adhesive wound dressings suitable for the present invention are disclosed in U.S. Pat. No. 5,827,213 to Jensen and U.S. Pat. No. 7,217,853 to Kulichikhin et al., the disclosures of which are incorporated herein by reference. A multi-layered composite dressing suitable for use in the present invention is the REPEL™ wound dressing available from MPM Medical, Inc. of Irving, Tex.

In use, the sacral wound should first be cleaned and prepared to receive a wound dressing, as is known in the art. The protective layer 53 of the wound dressing 15 is removed to expose the adhesive layer 50 and the absorbent layer 52, the wound dressing 15 is folded over on itself substantially along a central axis A running from the top end 20 to the bottom end 30 of the wound dressing 15 so that the adhesive layer 50 and the absorbent layer 52 are outwardly oriented (see FIG. 6), the medial projection 33 of the wound dressing 15 is inserted into a superior portion of the gluteal cleft of the person 10 to adhere the medial projection 33 to the skin of the person 10 within the gluteal cleft, the lateral projections 31, 32 of the wound dressing 15 are then pushed against a superior portion of the buttocks of the person 10 to adhere the lateral projections 31, 32 to the skin of the person 10, and the opposing lateral ends 40, 45 and the top end 20 of the wound dressing 15 are then pushed against the skin of the person 10 until the wound dressing 15 is properly adhered to the sacrococcygeal region 11 of the person 10 over the sacral wound. The wound dressing 15 is reversibly adhered to the skin, thus the wound dressing 15 can be repeatedly peeled back to inspect the wound and then resealed over the wound.

The wound dressing 15 may be made in various sizes and dimensions to accommodate people of various sizes and shapes. The absorbent layer 52 can vary in size and shape, but an uninterrupted border (e.g. 0.5 to 1.0 inch) of the adhesive layer 50 should be exposed to provide a proper seal around the sacral wound and thereby prevent contaminants from invading the area protected by the wound dressing 15. The wound dressing 15 provides a cushioning effect and, therefore, can also be used to prevent the development of a pressure sore or worsening of a minor pressure sore into an open wound.

While the invention has been shown and described in some detail with reference to a specific exemplary embodiment, there is no intention that the invention be limited to such detail. On the contrary, the invention is intended to include any alternative or equivalent embodiments that fall within the spirit and scope of the invention as described above and as recited in the appended claims.

The invention claimed is:

1. A method of applying a tulip-shaped wound dressing over a sacral wound in the sacrococcygeal region of a person, said tulip-shaped wound dressing comprising a top end, a bottom end, opposing lateral ends, an adhesive layer, a backing layer adjacent said adhesive layer on an exterior side thereof, an absorbent layer adjacent said adhesive layer on an interior side thereof, and a removable protective layer attached to said adhesive layer on said interior side thereof and covering said absorbent layer, wherein said top end of said tulip-shaped wound dressing comprises two arcuate lobes in sequence and said bottom end has two lateral projections and a medial projection positioned between the two lateral projections at a central region of said bottom end, wherein said medial projection and said two lateral projections of said tulip-shaped wound dressing are V-shaped; said method comprising the steps of:
   a) removing said protective layer to expose an uninterrupted border of said adhesive layer and said absorbent layer;
   b) folding said tulip-shaped wound dressing along a central axis running from said top end to said bottom end of said tulip-shaped wound dressing so that said adhesive layer and said absorbent layer are outwardly oriented;
   c) inserting said medial projection of said tulip-shaped wound dressing into a superior portion of the gluteal cleft of the person to adhere said medial projection to the skin of the person within the gluteal cleft;
   d) pushing said two lateral projections of said tulip-shaped wound dressing against a superior portion of the buttocks of the person to adhere said two lateral projections to the skin of the person; and
   e) pushing said opposing lateral ends and said top end of said tulip-shaped wound dressing against the skin of the person until said tulip-shaped wound dressing is adhered to the sacrococcygeal region of the person over the sacral wound;
   f) wherein said step of inserting said medial projection is performed before said steps of pushing said two lateral projections and pushing said opposing lateral ends and said top end against the skin of the person to anchor said medial projection to the skin within the gluteal cleft prior to adhering said two lateral projections, said opposing lateral ends, and said top end to the skin;
   g) wherein the tulip-shaped wound dressing further comprises spaces between said medial projection and said two lateral projections wherein the spaces allow said bottom end of said tulip-shaped wound dressing to flex during body movement and thereby prevent inadvertent detachment of the tulip-shaped wound dressing from the skin.

2. A method according to claim 1, wherein said two lateral projections of said tulip-shaped wound dressing are coextensive and a maximum length of said two lateral projections is greater than a maximum length of said medial projection.

3. A method according to claim 1, wherein the central axis running from said top end to said bottom end of said tulip-shaped wound dressing divides said tulip-shaped wound dressing into first and second sides, wherein said first side is opposite from said second side and said first side is a mirror image of said second side.

4. A method of applying a tulip-shaped wound dressing over a sacral wound in the sacrococcygeal region of a person, said tulip-shaped wound dressing comprising top end, a bottom end, opposing lateral ends, an absorbent adhesive layer, a backing layer adjacent said absorbent adhesive layer on an exterior side thereof, and a removable protective layer attached to said absorbent adhesive layer on an interior side thereof, wherein said top end of said tulip-shaped wound dressing comprises two arcuate lobes in sequence and said bottom end has two lateral projections and a medial projection positioned between the two lateral projections at a central region of said bottom end, wherein said medial projection and said two lateral projections of said tulip-shaped wound dressing are V-shaped; said method comprising the steps of:
  a) removing said protective layer to expose said absorbent adhesive layer;
  b) folding said tulip-shaped wound dressing along a central axis running from said top end to said bottom end of said tulip-shaped wound dressing so that said absorbent adhesive layer is outwardly oriented;
  c) inserting said medial projection of said tulip-shaped wound dressing into a superior portion of the gluteal cleft of the person to adhere said medial projection to the skin of the person within the gluteal cleft;
  d) pushing said two lateral projections of said tulip-shaped wound dressing against a superior portion of the buttocks of the person to adhere said two lateral projections to the skin of the person; and
  e) pushing said opposing lateral ends and said top end of said tulip-shaped wound dressing against the skin of the person until said tulip-shaped wound dressing is adhered to the sacrococcygeal region of the person over the sacral wound;
  f) wherein said step of inserting said medial projection is performed before said steps of pushing said two lateral projections and pushing said opposing lateral ends and said top end against the skin of the person to anchor said medial projection to the skin within the gluteal cleft prior to adhering said two lateral projections, said opposing lateral ends, and said top end to the skin;
  g) wherein the tulip-shaped wound dressing further comprises spaces between said medial projection and said two lateral projections wherein the spaces allow said bottom end of said tulip-shaped wound dressing to flex during body movement and thereby prevent inadvertent detachment of the tulip-shaped wound dressing from the skin.

5. A method according to claim 4, wherein said two lateral projections of said tulip-shaped wound dressing are coextensive and a maximum length of said two lateral projections is greater than a maximum length of said medial projection.

6. A method according to claim 4, wherein the central axis running from said top end to said bottom end of said tulip-shaped wound dressing divides said tulip-shaped wound dressing into first and second sides, wherein said first side is opposite from said second side and said first side is a mirror image of said second side.

* * * * *